United States Patent
Roy et al.

(10) Patent No.: US 12,064,356 B2
(45) Date of Patent: Aug. 20, 2024

(54) MULTI-SIZE ACETABULAR IMPACTOR

(71) Applicant: Howmedica Osteonics Corp., Mahwah, NJ (US)

(72) Inventors: Shammodip Roy, Wayne, NJ (US); Matthew P. Abdel, Rochester, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 182 days.

(21) Appl. No.: 17/891,390

(22) Filed: Aug. 19, 2022

(65) Prior Publication Data

US 2023/0057126 A1  Feb. 23, 2023

Related U.S. Application Data

(60) Provisional application No. 63/234,794, filed on Aug. 19, 2021.

(51) Int. Cl.
*A61F 2/46* (2006.01)
*A61F 2/30* (2006.01)
*A61F 2/34* (2006.01)

(52) U.S. Cl.
CPC ........ *A61F 2/4609* (2013.01); *A61F 2/30771* (2013.01); *A61F 2/34* (2013.01); *A61F 2002/30784* (2013.01); *A61F 2002/3093* (2013.01); *A61F 2002/3448* (2013.01); *A61F 2002/3483* (2013.01); *A61F 2002/4681* (2013.01)

(58) Field of Classification Search
CPC ........ A61F 2/34; A61F 2/4603; A61F 2/4609; A61B 17/90; A61B 17/92
See application file for complete search history.

(56) References Cited

U.S. PATENT DOCUMENTS

| 5,431,657 A | 7/1995 | Rohr |
| 5,571,200 A | 11/1996 | Cohen et al. |
| 6,743,235 B2 | 6/2004 | Subba Rao |

(Continued)

FOREIGN PATENT DOCUMENTS

| AU | 2008247066 A1 | 11/2008 |
| CA | 2528461 C | 4/2014 |

(Continued)

*Primary Examiner* — Brian A Dukert
(74) *Attorney, Agent, or Firm* — Lerner David LLP

(57) ABSTRACT

An acetabular implant kit includes a first acetabular component that has an inner surface that defines a first concave profile. A second acetabular component includes an inner surface that defines a second concave profile. An instrument includes an elongated body that has a first end and a second end. A head is connected to the second end of the body and has an engagement surface. The engagement surface includes a first convex profile and a second convex profile. The first and second convex profiles are arranged along a longitudinal axis of the head and have a first radius of curvature configured to congruently engage the first concave profile of the first acetabular component. The second convex profile has a second radius of curvature configure to congruently engage the second concave profile of the second acetabular component. The first radius of curvature is different than the second radius of curvature.

20 Claims, 2 Drawing Sheets

(56) References Cited

U.S. PATENT DOCUMENTS

| | | |
|---|---|---|
| 7,247,158 B2 | 7/2007 | Harris, Jr. |
| 7,341,593 B2 | 3/2008 | Auxepaules et al. |
| 7,727,282 B2 | 6/2010 | Slone et al. |
| 7,931,656 B2 | 4/2011 | Parry et al. |
| 8,277,457 B1 | 10/2012 | Burgi et al. |
| 8,398,650 B1 | 3/2013 | Burgi |
| 8,535,324 B2 | 9/2013 | Aux Epaules et al. |
| 8,834,479 B2 | 9/2014 | Aux Epaules et al. |
| 8,894,660 B2 | 11/2014 | Aux Epaules et al. |
| 8,926,621 B2 | 1/2015 | Liang |
| 8,936,604 B2 * | 1/2015 | Mani ............ A61F 2/4607 606/100 |
| 8,961,528 B2 | 2/2015 | Burgi |
| 9,119,731 B2 | 9/2015 | Burgi et al. |
| 9,289,313 B2 | 3/2016 | Preuss et al. |
| 9,345,585 B2 | 5/2016 | Black |
| 9,463,093 B2 | 10/2016 | Allen et al. |
| 10,092,420 B2 | 10/2018 | Kerboul et al. |
| 10,307,267 B2 | 6/2019 | Pritchett |
| 10,398,570 B2 | 9/2019 | Gradel |
| 10,588,756 B2 | 3/2020 | Schmit |
| 10,596,011 B2 | 3/2020 | Beck et al. |
| 10,695,193 B2 | 6/2020 | Bailey et al. |
| 10,722,382 B2 | 7/2020 | Termanini et al. |
| 2008/0021568 A1 | 1/2008 | Tulkis et al. |
| 2012/0239160 A1 | 9/2012 | Belew et al. |
| 2016/0100957 A1 | 4/2016 | Lewis |

FOREIGN PATENT DOCUMENTS

| | | |
|---|---|---|
| EP | 2572679 B1 | 7/2015 |
| WO | 2012028182 A1 | 3/2012 |
| WO | 2014108540 A1 | 7/2014 |
| WO | 2018031752 A1 | 2/2018 |
| WO | 2019015962 A1 | 1/2019 |
| WO | 2021110699 A2 | 6/2021 |

* cited by examiner

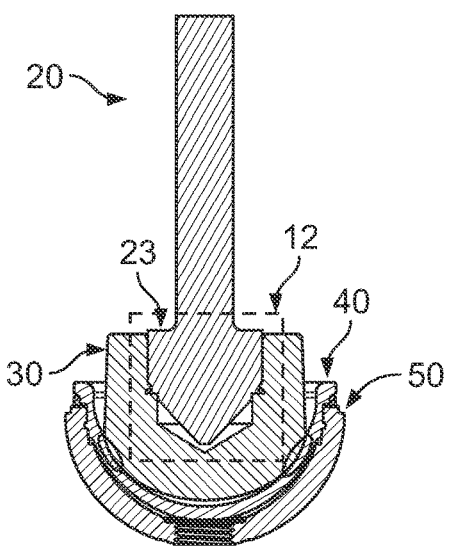
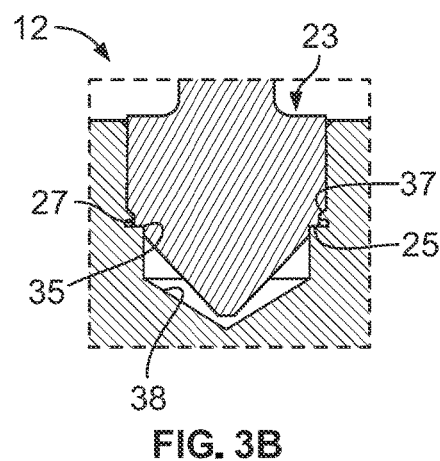
FIG. 3A
FIG. 3B
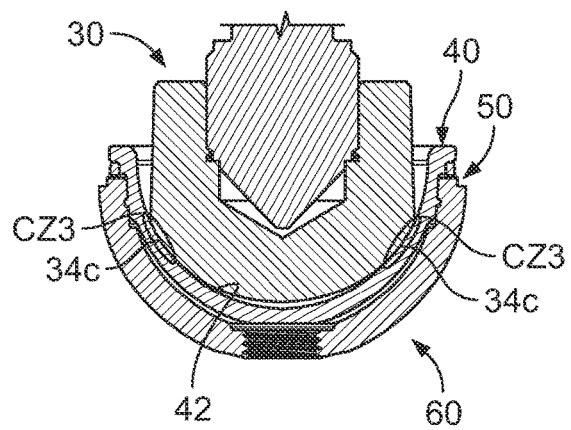
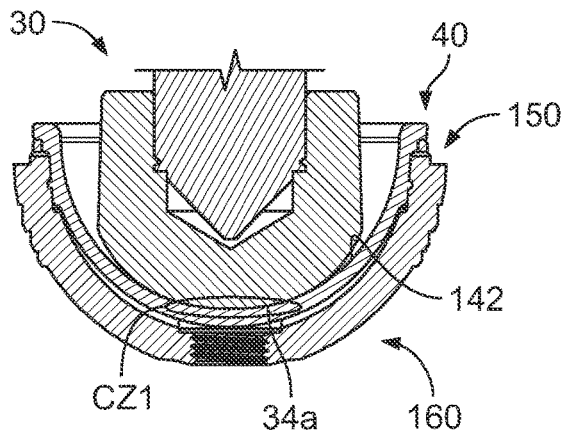
FIG. 3C
FIG. 4

MULTI-SIZE ACETABULAR IMPACTOR

CROSS-REFERENCE TO RELATED APPLICATIONS

This application claims the benefit of the filing date of U.S. Provisional Patent Application Ser. No. 63/234,794, filed Aug. 19, 2021, the disclosure of which is hereby incorporated by reference.

BACKGROUND OF THE INVENTION

Hip arthroplasty is generally understood to be the replacement of a hip joint with an artificial joint. During hip replacement, a femoral head is typically resurfaced or resected from a proximal femur and subsequently replaced with a prosthetic implant, which is usually a metal or ceramic spherical construct of similar size and shape. Correspondingly, an acetabulum is prepared by reshaping the acetabulum and implanting an acetabular implant into the reshaped acetabulum. The acetabular implant mates with the prosthetic femoral head for articulation of the artificial joint.

Acetabular implants typically include a shell and a liner. The shell is usually received within the reshaped acetabulum and is often secured to the bone via press-fit, bone cement, and/or bone screws. The liner is commonly received within the shell and forms one or more bearing surfaces for hip joint articulation. Acetabular shells are often impacted into a prepared acetabulum, even when using bone cement, to fully seat the shell in the bone. Acetabular liners may similarly be impacted into the acetabular shell in order to seat the liner in the shell, which is typically a press-fit relationship.

Insertion and impaction is often performed by an inserter-impactor tool. Since most shells and liners have a hemispherical shape, inserter-impactor tools are usually specifically designed to a particular size shell or liner in order to evenly distribute impaction forces to ensure proper seating and orientation of the device being impacted. Since a typical surgical kit includes multiple sized shells and liners, such kit correspondingly includes multiple inserter-impactor tools, or modular components thereof. However, each additional instrument that is included in the kit increases logistical costs, clutter in the operating theatre and the potential for infection. Therefore, further improvements are desirable.

BRIEF SUMMARY OF THE INVENTION

The present disclosure generally describes a multi-size inserter impactor tool. Such inserter-impactor tool has a head configured to engage multiple sizes of acetabular liners or shells so that a single tool can be used for each of such sizes.

In one aspect of the present disclosure, an acetabular implant kit includes a first acetabular component that has an inner surface that defines a first concave profile. A second acetabular component includes an inner surface that defines a second concave profile. The kit also includes an instrument which includes an elongated body that has a first end and a second end. A head is connected to the second end of the body and has an engagement surface. The engagement surface includes a first convex profile and a second convex profile. The first and second convex profiles are arranged along a longitudinal axis of the head and have a first radius of curvature configured to congruently engage the first concave profile of the first acetabular component. The second convex profile has a second radius of curvature configure to congruently engage the second concave profile of the second acetabular component. The first radius of curvature is different than the second radius of curvature.

Additionally, the kit may include a third acetabular component that has an inner surface that defines a third concave profile. The engagement surface may further include a third convex profile. The third convex profile may have a third radius of curvature configured to congruently engage the inner surface of the third acetabular component and may have a third radius of curvature different than the first and second radii of curvature. The first convex profile may intersect the longitudinal axis of the head. Also, the second and third convex profiles may extend about the longitudinal axis of the head. The second and third convex profiles may be ring-shaped, and the first convex profile may be dome-shaped. The second convex profile may be tangent to the first and third convex profiles. The second radius of curvature may be smaller than the first radius of curvature, and the third radius of curvature may be smaller than the second radius of curvature.

Continuing with this aspect, the first radius of curvature of the first convex profile may be larger than the second radius of curvature of the second convex profile. The first convex profile may be centrally located on the head. The first and second convex profiles may be ring shaped and may extend about the longitudinal axis of the head.

Furthermore, the first acetabular component may be a first acetabular liner configured to be received within an acetabular shell of a first size, and the second acetabular component may be a second acetabular liner configured to be received within a second acetabular shell of a second size smaller than the first size. The second convex profile of the head may be configured so that it is free from engagement with the inner surface of the first acetabular component when the first convex profile of the head congruently engages the first concave profile, and the first convex profile may be configured so that it is free from engagement with the inner surface of the second acetabular component when the second convex profile of the head congruently engages the second concave profile.

Additionally, the first inner surface of the first acetabular component may define a first hemispherical cavity that has a first diameter, and the second inner surface of the first acetabular component may define a second hemispherical cavity that has a second diameter smaller than the first diameter. The first and second acetabular components may each be an acetabular shell that has a porous outer surface configured to promote bone ingrowth. Alternatively, the first acetabular component may be an acetabular shell, and the second acetabular component may be an acetabular liner configured to be received within the first hemispherical cavity of the first acetabular component.

According to another aspect of the present disclosure, an acetabular inserter instrument includes an elongated body that has a first and second ends, and a head that is connected to the second and has a convex outer surface. The convex outer surface of the head has first and second engagement portions that extend at least partially about and partially along an axis of the head. The first engagement portion has a first radius of curvature different than a second of curvature of the second engagement portion.

Additionally, the first radius of curvature may be greater than the second radius of curvature. Also, the first engagement portion may be centrally located on the head such that it intersects the axis of the head, and the second engagement portion may be tangent to the first engagement portion. The head may be detachably coupled to the first end of the elongated body.

According to a further aspect of the present disclosure, a method for implanting a prosthetic acetabular implant includes selecting one of a first acetabular component and a second acetabular component from a plurality of acetabular components. The first acetabular component is of a different size than the second acetabular component. When first acetabular component is selected, a first concave profile of an inner surface of the first acetabular component is engaged with a first convex profile of a head of an inserter instrument. When the second acetabular component is selected, a second concave profile of an inner surface of the second acetabular component is engaged with a second convex profile of the head so that the first convex profile of the head is free from engagement with the second acetabular component. The method also includes inserting the selected acetabular component into a prepared acetabulum of a mammalian subject using the inserter instrument.

BRIEF DESCRIPTION OF THE DRAWINGS

The features, aspects, and advantages of the present invention will become better understood with regard to the following description, appended claims, and accompanying drawings in which:

FIG. 3A is a cross-sectional view of the inserter instrument of FIG. 1 engaged with a first acetabular implant.

FIG. 3B is an enhanced cross-sectional view of a connection mechanism of the inserter-impactor tool of FIG. 1.

FIG. 3C is an enhanced cross-sectional view of the head of FIG. 2A engaged with the first acetabular implant.

FIG. 4 is an enhanced cross-sectional view of the head of FIG. 2A engaged with a second acetabular implant.

DETAILED DESCRIPTION

Figure 1:
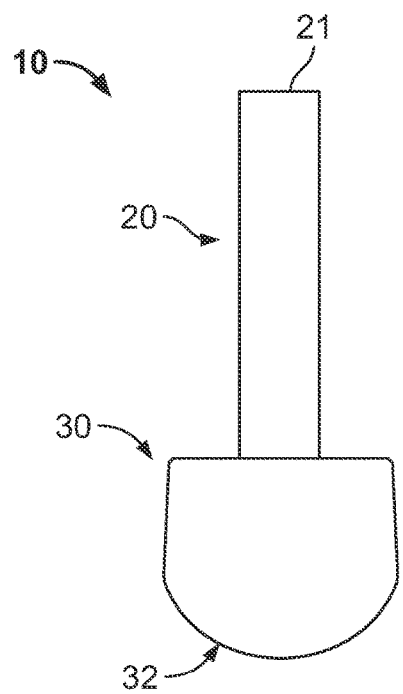
FIG. 1 is a front elevational view of an inserter instrument according to an embodiment of the present disclosure.

FIGS. 1-4 depict an inserter instrument 10 according to an embodiment of the present disclosure. Instrument 10 generally includes an elongate body or shaft 20 and a head 30. Inserter instrument 10 is configured to dynamically insert, such as through impaction, an acetabular implant component into bone or into a cavity of another acetabular component. While the present disclosure discusses inserter instrument 10 in conjunction with acetabular implants and components thereof, it should be understood that the subject matter described herein is also applicable to implants utilized in other joints of the mammalian body, such as the glenohumeral joint.

Shaft 20 connects to head 30, as described further below, and may be used to position and apply impact forces to head 10. In this regard, shaft 20 has an impaction end 21 configured to be impacted by a mallet and the like and a connection end 23 configured to connect to head 30. Shaft 20 is preferably made from a biocompatible material capable of withstanding push and impaction forces. For example, shaft may be made of stainless steel, titanium, cobalt chromium, and the like. Shaft 20 may be configured as a straight cylindrical or rectangular shaft. However, shaft 20 can also be non-linear. For example, shaft 20 may have an offset (not shown) such that shaft 20 has at least two axes offset from each other. Additionally, exemplary embodiments of the shaft 20 may include handles, knobs, and/or protruding elements designed to assist the user with the insertion and impaction.

Head 30 general includes a first side and second side. The first side includes a cavity that is defined by an inner surface 38 and is configured to connect to connection end 23 of shaft 20. In the embodiment depicted, shaft 20 connects to the head 10 via a connection mechanism 12 which is a threaded connection. In this regard, inner surface 38 defines one or more projections or threads 37 which engage corresponding projections or threads 27 on connection end 23 of shaft 20 for a threaded arrangement, as best shown in FIGS. 3A and 3B. Alternatively, the head 10 and shaft 20 may be configured to be connected together with other means such as, but not limited to, clamping or through a quick-connect mechanism, such as a ball-detent or snap-fit arrangement. It is also contemplated that shaft 20 and head 30 may be integral with each other so as to form a monolithic structure. Thus, connection mechanism 12 between head 30 and shaft 20 may be permanent or semi-permanent (e.g., detachable connection). Although head 30 and shaft 20 are connected via threads 27, 37, both head and connection end 23 of shaft 20 have a circumferential ledge or shoulder 25, 35 located distal to threads 27, 37. Such ledges 25, 35 abut each other when head 30 and shaft 20 are fully connected. During impaction, load is transferred through the flat-on-flat planar interface created by this abutment rather than through threads 27, 37 thereby ensuring even load transfer and that the threaded connection is not damaged.

Figure 2A:
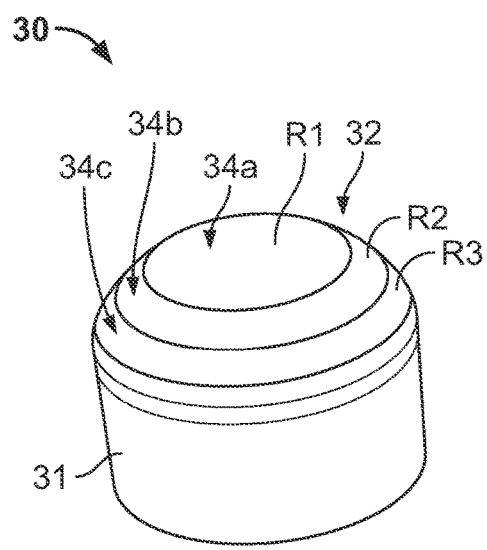
FIG. 2A is a perspective view of a head of the inserter instrument of FIG. 1.
Figure 2B:
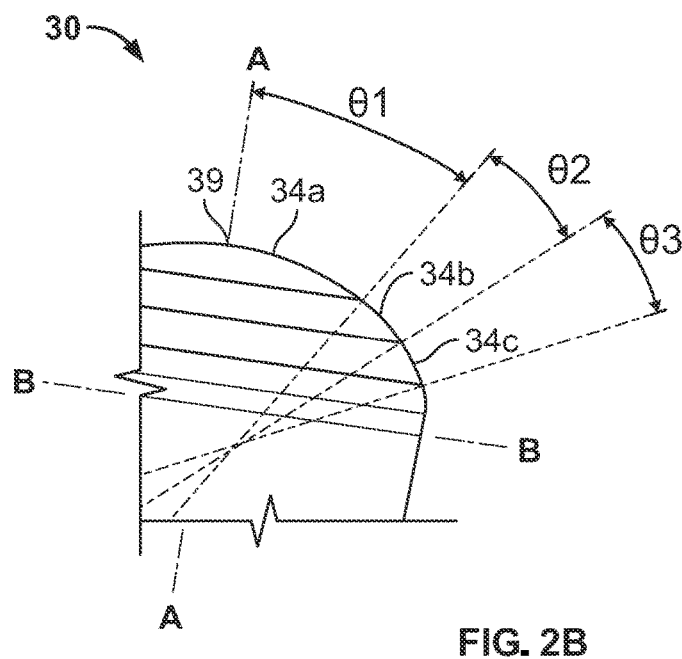
FIG. 2B is a partial perspective view of the head of FIG. 2A.

The second side of head 30 includes a first portion 31 and a second portion 32. First portion 31 is a cylindrical or frustoconical. Second portion 32 extends from first portion 31 and is an outer convex engagement surface that includes a plurality of convex profiles or surfaces 34a-c. Each of the convex profiles 34a-c are spherical and have a corresponding spherical radius of curvature R1-R3 which differs for each convex profile 34a-c. In this regard, head 30 is configured to conform to multiple differently sized implants, as discussed further below. The embodiment depicted includes a first, second, and third convex profile 34a-c. Each convex profile 34a-c is concentric about an axis A which intersects first convex profile 34a, as shown in FIG. 2B. In this regard, first convex profile 34a forms a dome and an apex 39 of convex engagement surface 32. Such apex 39 lies on axis A. Second convex profile 34b is tangent to first convex profile 34a and forms a spherical ring that extends entirely about and concentric with axis A. Third convex profile 34c is tangent to second convex profile 34b and also extends entirely about and concentric with axis A. Thus, second convex profile 34b is disposed between first and third convex profiles 34a, 34c such that there is an uninterrupted transition from one convex profile to the next.

Each of convex profiles 34a-c is configured to congruently engage a corresponding concave surface in an acetabular component such as an acetabular shell or liner. In this regard, the radius of curvature R1-R3 of a profile 34 is generally configured for a particularly sized acetabular component so that congruent surface-to-surface contact can be established. Thus, the first radius of curvature R1 associated with first convex profile 34a is configured for a first size acetabular component, the second radius of curvature R2 associated with second convex profile 34b is configured for a second size acetabular component, and the third radius of curvature R3 associated with third convex profile 34c is configured for a third size acetabular component. In order to ensure that the appropriate convex profile 34a-c only interacts with the intended implant, the radii of curvature R1-R3 progressively decrease from axis A. In this regard, R1 is greater than R2 which is greater than R3. As an example, R1 may be 21 mm, R2 may be 19 mm, and R3 may be 14 mm. Thus, the radii of curvature of engagement surface 32 generally decreases from first convex profile 34a to third convex profile 34c such that R1 corresponds with the largest acetabular component while R3 corresponds with the smallest acetabular component.

FIGS. 3C and 4 illustrate congruent contact with differently sized acetabular implants 60 and 160. Such acetabular implants each include one more acetabular components which can be, for example, an acetabular liner 40, 140 and/or acetabular shell 50, 150. Such components 40, 50, 140, 150 typically have concave cavities which are defined by corresponding concave surfaces which are generally spherical such that they each have a spherical radius of curvature. In this regard, a kit of acetabular implants may include several acetabular shells and acetabular liners of various sizes each with a different radius of curvature. As shown in FIG. 3C, a concave surface 42 of acetabular liner 40 of a first size is engaged by third convex profile 34c to form a third congruent contact zone CZ3 between a portion of concave surface 42 and third convex profile 34c. Such congruent contact zone CZ3 is an area of contact between third convex profile 34c and concave surface 42. In this regard, congruent contact zone CZ3 is ring or annulus shaped which matches the ring/annulus shape of third convex profile 34c. As such, engagement between head 30 and concave surface 42 is area contact, as opposed to point or line contact, which is concentric about axis A. This helps self-center head 30 within acetabular component 40 and provide even distribution of insertion forces.

As shown in FIG. 4, second acetabular implant 160 includes a liner 140 and shell 150. Liner 140 and shell 150 are of a larger size than that of first acetabular implant 60. Thus, when head 30 is inserted into liner 140, or shell 150, there is clearance between second and third convex profiles 34b-c so that head 30 reaches all the way into the cavity of liner 140 so that first convex profile 34a contacts concave surface 142 of liner 140 thereby forming a first congruent contact zone CZ1. CZ1 unlike CZ3 is not ring shaped, but rather domical in correspondence with the dome shape of first convex profile 34a. However, just as with third convex profile 34c, first convex profile 34a self-centers and provides even distribution of insertion forces. It should be understood that a second congruent contact zone (not shown) can be formed with another acetabular implant of an intermediate size relative to first and second acetabular implants 60, 160.

In addition to having a spherical radius of curvature, each convex profile 34a-c has an angular span Θ that extends partially between the polar axis A and a transverse axis B, which is perpendicular to axis A, as shown in FIG. 2B. Thus, first convex profile 34a has a first angular span Θ1, second convex profile 34b has a second angular span Θ2, and third convex profile 34c has a third angular span Θ3. First angular span Θ1 is greater than second angular span Θ2 which is greater than third angular span Θ3. The angular spans Θ1, Θ2, Θ3 reduce non-linearly from axis A to axis B. In other words, the difference of first angular span Θ1 and second angular span Θ2 is greater than the difference of second angular span Θ2 and third angular span Θ3. For example, angular spans Θ1, Θ2, Θ3 may be about 30 degrees, 19 degrees, and 16 degrees, respectively. Distributing the radii of curvatures R1-R3 and angular spans Θ1, Θ2, Θ3 in this manner enables preferential contact between a concave surface of an acetabular component and a corresponding convex profile 34a-c of inserter head 30 thereby allowing the other non-corresponding profiles to simultaneously clear any contact or engagement. In addition, by adjusting the rate of decrease in angular spans Θ1, Θ2, Θ3 of the spherical radii of curvature R1-R3 from first convex profile 34a-c in a non-linear fashion as mentioned allows for the surface of area of contact to remain proportionally the same for each acetabular component size when engaged with head 30.

It is preferable that head 30 have three convex profiles 34 as this is allows head 30 to engage multiple size acetabular components while allowing for a larger contact area than a head with more convex profiles. However, it should be understood that at a minimum, convex engagement surface 32 of head 40 includes two convex profiles 34 that are concentrically arranged about axis A, such that the first profile is centrally located on the convex engagement surface 31 of the head 30. It should also be understood that head can include upwards of five convex profiles 34 for engagement with five differently sized acetabular components.

In addition, while the herein described convex profiles 34a-c of head 20, particularly second and third convex profiles 34b-c, are continuous about axis A, some embodiments may include convex profiles 34 that are interrupted along their circumference such as by grooves or otherwise the absence of structure. For example, head 30 may include multiple curved arms (not shown) symmetrically arranged about axis A and extending downward from axis A. Each of such arms may be separated from adjacent arms by a distance. Each arm may have a convex profile 34 so that the effect is an interrupted convex profile similar to the continuous convex profiles 34a-c of head 30 that is still capable of engaging an inner surface of an acetabular component for insertion.

Also, while first, second and third convex profiles 34a-c are tangent to each other, some embodiments of head 30 may have a space between one or more pairs of profiles 34. For example, head 30 can have a circumferential grooves separating each profile 34 from each other by a predetermined distance.

The multi-size acetabular inserter instrument 10 may be configured to perform various methods and procedures. Exemplary embodiments of the multi-size acetabular inserter instrument 10 with a head 30 may be configured to perform various insertion and impaction procedures such as, but not limited to, trialing an implant, reuse for a new implant, and/or pre-impaction of a liner into a shell. The multi-size inserter instrument 10 having a head 30 that engages an acetabular concave component with congruent surface-to-surface contact provides the operator optimal control over positioning and impacting of a component that defines a concave profile. Once a head 30 engages an acetabular component, inserter instrument 10 may be configured to apply a load onto the surface of the acetabular component.

Exemplary embodiments may include an acetabular implant kit that may be comprised of, but not limited to, a multi-size acetabular inserter instrument 10 with a shaft 20 and head 30, a first acetabular component having a first concave profile, a second acetabular component having second concave profile, and a third acetabular component having a third concave profile. Head 30 has convex engagement surface 32 that includes multiple convex profiles 34, such as profiles 34a-c, that are configured to conform to the concave profiles of the respective acetabular components. The acetabular components in the implant kit may be configured for cemented or cement-less placement. The acetabular components may be made from materials such as, but not limited to, plastic, ceramic, or metal. An exemplary embodiment of the acetabular implant kit may have acetabular components that are acetabular shells and liners, such that the acetabular liner may be configured for placement into the acetabular shell pre-impaction or post-impaction. Alternatively, the acetabular implant kit may have acetabular components that are only acetabular shells or acetabular liners of various sizes and materials. For example, an exemplary embodiment of the acetabular implant kit may include, but not limited to, acetabular shells having a porous outer surface configured to promote bone growth when implanted.

An exemplary embodiment of the acetabular implant kit may include methods of use. For example, a first acetabular component, which may be an acetabular shell, and a second acetabular component, which may be an acetabular liner, are selected out of a group of similar acetabular components comprising various sizes. The first acetabular component may be engaged with inserter 10 and impacted into a prepared acetabulum either in a press-fit manner or with bone cement. The second acetabular component is also engaged with inserter 10 and impacted into the first acetabular component to form the acetabular implant.

Should a third and/or fourth acetabular component of another size be selected, such as for example because it was determined through trialing of the first and second acetabular components that such components are either too big or too small, inserter 10 with the same inserter head 30 can be used in conjunction with the third and fourth acetabular component without the need to swap heads or inserter instruments. Thus, inserter 10 reduces the total number of instruments needed to perform a surgical procedure as inserter 10 can be used for a variety of implants, whether they be a trial implant or final implant.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular implant kit comprising:
a first acetabular component having an inner surface defining a first concave profile;
a second acetabular component having an inner surface defining a second concave profile; and
an inserter instrument comprising:
an elongated body having a first end and a second end; and
a head connected to the second end of the body and having an engagement surface, the engagement surface having a first convex profile and a second convex profile, the first and second convex profiles being arranged along a longitudinal axis of the head and having a first radius of curvature configured to congruently engage the first concave profile of the first acetabular component, the second convex profile having a second radius of curvature configure to congruently engage the second concave profile of the second acetabular component, the first radius of curvature being different than the second radius of curvature.

2. The acetabular implant kit of claim 1, further comprising a third acetabular component having an inner surface defining a third concave profile, wherein the engagement surface further includes a third convex profile, the third convex profile having a third radius of curvature configured to congruently engage the inner surface of the third acetabular component and having a third radius of curvature different than the first and second radii of curvature.

3. The acetabular implant kit of claim 2, wherein the first convex profile intersects the longitudinal axis of the head.

4. The acetabular implant kit of claim 3, wherein the second and third convex profiles extend about the longitudinal axis of the head.

5. The acetabular implant kit of claim 4, wherein the second and third convex profiles are ring-shaped and the first convex profile is dome-shaped.

6. The acetabular implant kit of claim 5, wherein the second convex profile is tangent to the first and third convex profiles.

7. The acetabular implant kit of claim 6, wherein the second radius of curvature is smaller than the first radius of curvature, and the third radius of curvature is smaller than the second radius of curvature.

8. The acetabular implant kit of claim 1, wherein the first radius of curvature of the first convex profile is larger than the second radius of curvature of the second convex profile.

9. The acetabular implant kit of claim 1, wherein the first convex profile is centrally located on the head.

10. The acetabular implant kit of claim 9, wherein the first and second convex profiles are ring shaped and extend about the longitudinal axis of the head.

11. The acetabular implant kit of claim 1, wherein the first acetabular component is a first acetabular liner configured to be received within an acetabular shell of a first size, and the second acetabular component is a second acetabular liner configured to be received within a second acetabular shell of a second size smaller than the first size.

12. The acetabular implant kit of claim 1, wherein, when the first convex profile of the head congruently engages the first concave profile, the second convex profile of the head is configured so that it is free from engagement with the inner surface of the first acetabular component, and when the second convex profile of the head congruently engages the second concave profile, the first convex profile is configures so that it is free from engagement with the inner surface of the second acetabular component.

13. The acetabular implant kit of claim 1, wherein the first inner surface of the first acetabular component defines a first hemispherical cavity having a first diameter, and the second inner surface of the first acetabular component defines a second hemispherical cavity having a second diameter smaller than the first diameter.

14. The acetabular implant kit of claim 1, wherein the first and second acetabular components are each an acetabular shell having a porous outer surface configured to promote bone ingrowth.

15. The acetabular implant kit of claim 14, wherein the first acetabular component is an acetabular shell, and the second acetabular component is an acetabular liner configured to be received within the first hemispherical cavity of the first acetabular component.

16. An acetabular inserter instrument comprising:
an elongated body having first and second ends; and
a head connected to the second end and having a convex outer surface, the convex outer surface having first and second engagement portions extending at least partially about and partially along an axis of the head, the first engagement portion having a first radius of curvature different than a second of curvature of the second engagement portion.

17. The acetabular inserter and impactor instrument of claim 16, wherein the first radius of curvature is greater than the second radius of curvature.

18. The acetabular inserter and impactor instrument of claim 17, wherein the first engagement portion is centrally located on the head such that it intersects the axis of the head, and the second engagement portion is tangent to the first engagement portion.

19. The acetabular inserter and impactor instrument of claim 18, wherein the head is detachably coupled to the first end of the elongated body.

20. A method for implanting a prosthetic acetabular implant comprising:
  selecting one of a first acetabular component and a second acetabular component from a plurality of acetabular components, the first acetabular component being of a different size than the second acetabular component;
  when the first acetabular component is selected, engaging a first concave profile of an inner surface of the first acetabular component with a first convex profile of a head of an inserter instrument;
  when the second acetabular component is selected, engaging a second concave profile of an inner surface of the second acetabular component with a second convex profile of the head so that the first convex profile of the head is free from engagement with the second acetabular component; and
  inserting the selected acetabular component into a prepared acetabulum of a mammalian subject using the inserter instrument.

* * * * *